(12) United States Patent
Jung et al.

(10) Patent No.: US 10,364,503 B2
(45) Date of Patent: Jul. 30, 2019

(54) MEDICAL GAS-LIQUID SUPPLY SYSTEM

(71) Applicant: YUAN ZE UNIVERSITY, Taoyuan (TW)

(72) Inventors: Guo-Bin Jung, Taoyuan County (TW); Chia-Chen Yeh, Miaoli County (TW); Jyun-Wei Yu, Taoyuan (TW); Chia-Ching Ma, Taoyuan (TW); Chung-Wei Hsieh, Tainan (TW)

(73) Assignee: YUAN ZE UNIVERSITY, Taoyuan (TW)

( * ) Notice: Subject to any disclaimer, the term of this patent is extended or adjusted under 35 U.S.C. 154(b) by 246 days.

(21) Appl. No.: 15/609,770

(22) Filed: May 31, 2017

(65) Prior Publication Data
US 2017/0362723 A1 Dec. 21, 2017

(30) Foreign Application Priority Data
Jun. 17, 2016 (TW) .............................. 105119126 A

(51) Int. Cl.
| | |
|---|---|
| *B01F 3/04* | (2006.01) |
| *C25B 1/13* | (2006.01) |
| *C25B 9/10* | (2006.01) |
| *A61K 33/00* | (2006.01) |
| *B01F 15/00* | (2006.01) |

(Continued)

(52) U.S. Cl.
CPC .............. *C25B 15/02* (2013.01); *A61K 33/00* (2013.01); *B01F 3/04985* (2013.01); *B01F 15/00422* (2013.01); *C25B 1/13* (2013.01); *C25B 9/10* (2013.01); *C25B 15/08* (2013.01); *B01F 2003/04879* (2013.01); *B01F 2003/04886* (2013.01); *B01F 2003/04914* (2013.01); *B01F 2215/0034* (2013.01); *Y02E 60/366* (2013.01)

(58) Field of Classification Search
CPC .... C25B 1/13; C25B 9/10; C25B 1/10; C25B 15/02; C25B 15/08; C02F 1/461–46104
See application file for complete search history.

(56) References Cited

U.S. PATENT DOCUMENTS

| | | | |
|---|---|---|---|
| 9,926,635 B2 * | 3/2018 | Jung ...................... | A01G 25/00 |
| 2017/0360070 A1 * | 12/2017 | Jung .................... | A23L 3/3445 |

FOREIGN PATENT DOCUMENTS

| | | |
|---|---|---|
| CN | 101388463 A | 3/2009 |
| CN | 101942668 A | 1/2011 |

(Continued)

*Primary Examiner* — Nicholas A Smith
(74) *Attorney, Agent, or Firm* — Li & Cai Intellectual Property (USA) Office

(57) ABSTRACT

A medical gas-liquid supply system including an electrolytic gas generator, a pure water supply device, a control unit, a first gas storing unit, a second gas storing unit and a gas output unit is provided. The control unit is electrically connected to the electrolytic gas generator for controlling the voltage value of the electrolytic gas generator and the type of gases generated by the electrolytic gas generator. The first and second gas storing units are communicated to the electrolytic gas generator for storing the first and second gases generated by the electrolytic gas generator respectively. The gas output unit is communicated to the first and second gas storing units and has first, second and third output ends for outputting the first gas, a mixed gas and the second gas respectively, in which the mixed gas includes the first and second gases.

13 Claims, 3 Drawing Sheets

(51) Int. Cl.
*C25B 15/02* (2006.01)
*C25B 15/08* (2006.01)

(56) References Cited

FOREIGN PATENT DOCUMENTS

| CN | 204959046 | * | 1/2016 | ............... | C25B 1/04 |
| CN | 204959046 U | | 1/2016 | | |
| TW | 201504476 | * | 2/2015 | ............... | C25B 1/04 |
| TW | 201504476 A | | 2/2015 | | |
| TW | I503171 B | * | 10/2015 | ............... | B01J 7/00 |
| TW | I503171 B | | 10/2015 | | |

\* cited by examiner

MEDICAL GAS-LIQUID SUPPLY SYSTEM

BACKGROUND

1. Technical Field

The instant disclosure relates to a medical gas-liquid supply system, in particular, to a medical gas-liquid supply system supplying hydrogen gas, oxygen gas, ozone or the mixed gas thereof.

2. Description of Related Art

Existing medical or therapy techniques prove that hydrogen gas, high pressure oxygen gas and ozone have benefits towards treatment of diabetes, cardiovascular disease, hearing impairment and spinal nerve diseases, etc. For example, hydrogen-rich water increases serum adiponectin and extra-cellular-superoxide dismutase (EC-SOD) and hence, can improve the condition of insulin resistance. In addition, hydrogen-rich water is effective to the lipid and glucose metabolism in the human body and can halt the progression of type two diabetes and insulin resistance.

In addition, ozone can reduce the blood sugar of the patient and increase the sensitivity toward insulin, thereby preventing vascular complications. High pressure oxygen is useful to treat wounds related to diabetes and does not have many side effects and hence, can be used on patients with amputation or patients in a life-threatening condition.

In the existing art, recombination processes are used to produce hydrogen gas. In the recombination process, steam and alcohols or hydrocarbons (ex. natural gas) used as fuel are reacted by the aid of recombination process catalysts for producing hydrogen gas. However, the hydrogen gas obtained by recombination processes has low purity and cannot be directly used as the required high purity hydrogen gas. In addition, the system of the recombination processes is relatively complicated.

The air separation process is used for producing oxygen gas. However, the oxygen gas obtained by the separation process has normal pressure and the system of the separation process is relatively complicated. The separation process comprises pressure swing adsorption (PSA), cryogenic, membrane separation steps. In addition, an ultraviolet process, a silent discharge process and a point discharge process are used to manufacture ozone.

However, the above ozone manufacturing processes include decomposing the oxygen molecule in the air to form an oxygen atom with negative charge. However, since air comprises a large amount of nitrogen, nitrogen is decomposed to form nitrogen oxides ($NO_x$), and these compounds tend to form nitrites which are harmful to the human body when combined with moisture in the air.

SUMMARY

The instant disclosure provides a medical gas-liquid system which uses a proton exchange membrane (PEM) technique to electrolyze water for generating hydrogen gas and oxygen gas, or generating hydrogen gas, oxygen gas and ozone.

One of the embodiments of the present disclosure provides a medical gas-liquid supply system, comprising an electrolytic gas generator, a pure water supply system, a control unit, a first gas storing unit, a second gas storing unit and a gas output unit. The pure water supply system is connected to the electrolytic gas generator for supplying water to the electrolytic gas generator. The control unit is electrically connected to the electrolytic gas generator, in which the control unit controls the voltage value of the electrolytic gas generator for controlling the type of gases generated by the electrolytic gas generator. The first gas storing unit is communicated to the electrolytic gas generator for storing a first gas output by the electrolytic gas generator. The second gas storing unit is communicated to the electrolytic gas generator for storing a second gas output by the electrolytic gas generator. The gas output unit is communicated to the first gas storing unit and the second storing unit, in which the gas output unit has a first output end for outputting the first gas, a second output end for outputting a mixed gas and a third output end for outputting the second gas, wherein the mixed gas comprises the first gas and the second gas.

To sum up, the medical gas-liquid supply system employs an electrolytic gas generator to electrolyze water, thereby generating hydrogen gas with high purity, oxygen gas with high pressure and ozone without $NO_x$. In addition, the control unit controls the voltage value of the electrolytic gas generator to adjust the type of gases generated by the electrolytic gas generator.

In order to further understand the techniques, means and effects of the instant disclosure, the following detailed descriptions and appended drawings are hereby referred to, such that, and through which, the purposes, features and aspects of the instant disclosure can be thoroughly and concretely appreciated; however, the appended drawings are merely provided for reference and illustration, without any intention to be used for limiting the instant disclosure.

BRIEF DESCRIPTION OF THE DRAWINGS

The accompanying drawings are included to provide a further understanding of the instant disclosure, and are incorporated in and constitute a part of this specification. The drawings illustrate exemplary embodiments of the instant disclosure and, together with the description, serve to explain the principles of the instant disclosure.

DESCRIPTION OF THE EXEMPLARY EMBODIMENTS

Figure 1:
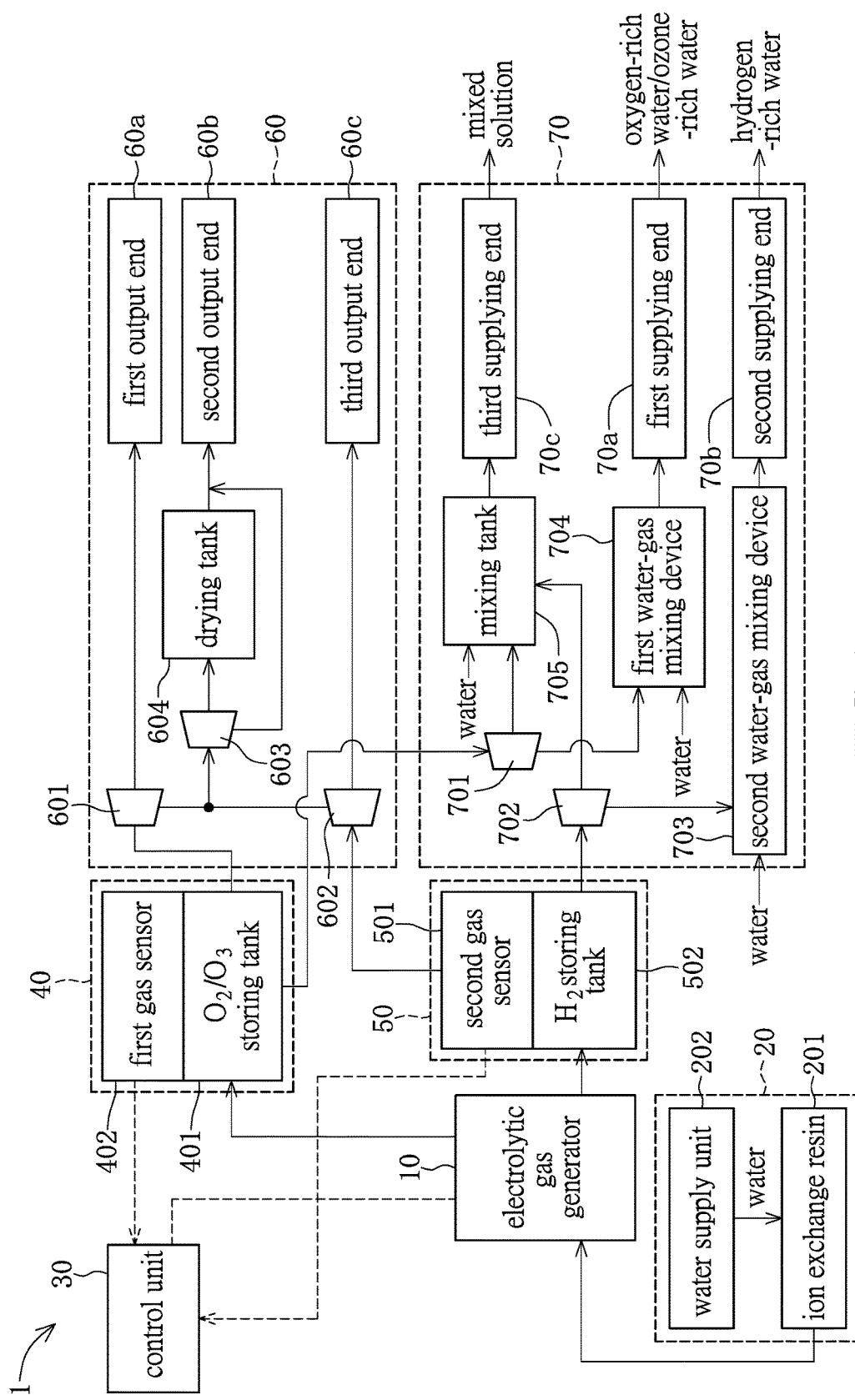
FIG. 1 is a function block diagram of the medical gas-liquid supply system of the embodiments of the instant disclosure.

Reference will now be made in detail to the exemplary embodiments of the instant disclosure, examples of which are illustrated in the accompanying drawings. Wherever possible, the same reference numbers are used in the drawings and the description to refer to the same or like parts.

FIG. 1 is a function block diagram of the medical gas-liquid supply system of the embodiments of the instant disclosure. The medical gas-liquid supply system 1 of the embodiments of the instant disclosure can provide hydrogen gas, oxygen gas, ozone or the combination thereof according to the actual medical use. In addition, the medical gas-liquid supply system 1 of the embodiments of the instant disclosure can provide hydrogen-rich water, oxygen-rich water, ozone-rich water or a mixed solution containing hydrogen gas, oxygen gas and ozone.

Specifically, the medical gas-liquid supply system 1 comprises an electrolytic gas generator 10, a pure water supply device 20, a control unit 30, a first gas storing unit 40, a second gas storing unit 50, a gas output unit 60 and a liquid output unit 70.

In the embodiments of the instant disclosure, the electrolytic gas generator 10 electrolyzes water to generate gases. Therefore, the pure water supply device 20 is communicated to the electrolytic gas generator 10 for supplying water to the electrolytic gas generator 10. In the present embodiment, the pure water supply device 20 comprises a water supply unit 202 and an ion exchange resin 201, in which water provided by the water supply unit 202 passes through the ion exchange resin 201 for removing the cations and anions dissolved in water, and water is supplied to the electrolytic gas generator 10. In an embodiment, the water supply unit 202 is a water storing tank or a water inlet pipeline.

Figure 2:
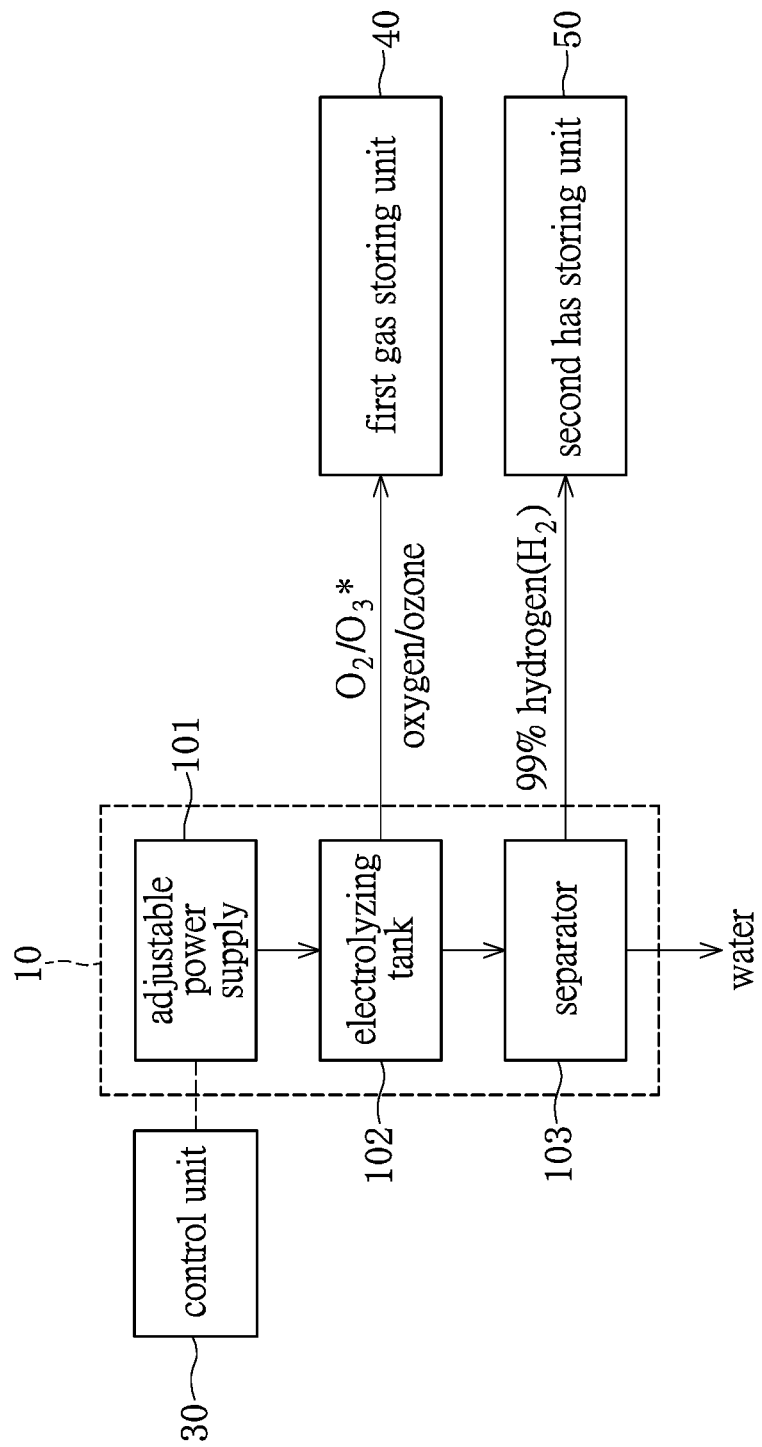
FIG. 2 is a function block diagram of the electrolytic gas generator of the embodiments of the instant disclosure.

In addition, the electrolytic gas generator 10 of the embodiments of the instant disclosure is a proton exchange membrane (PEM) electrolytic gas generator. Please refer to FIG. 2. FIG. 2 is a function block diagram of the electrolytic gas generator of the embodiments of the instant disclosure. The electrolytic gas generator 10 of the embodiments of the instant disclosure comprises an electrolytic gas generator 10, an electrolyzing tank 102 and a separator 103.

Figure 3:
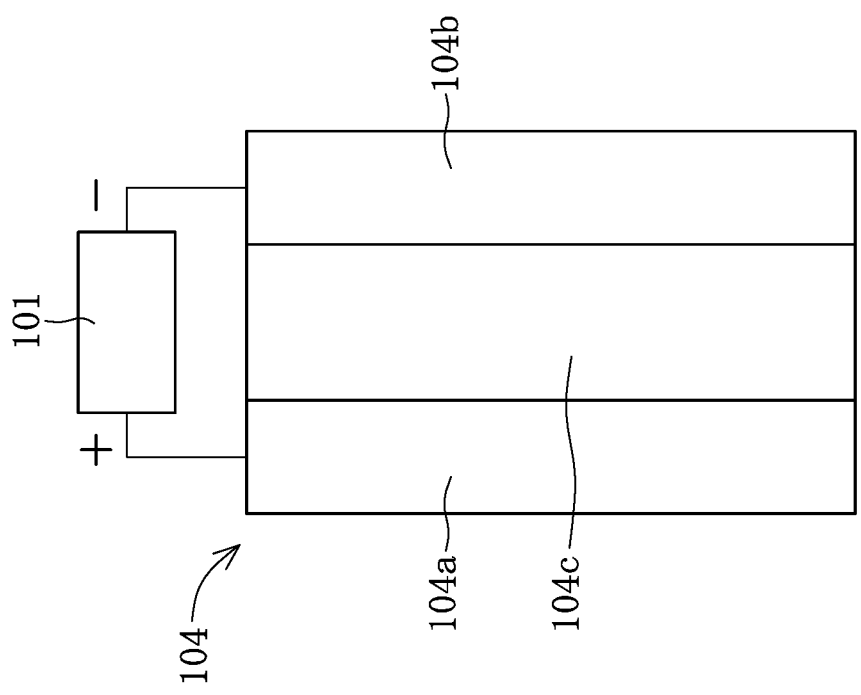
FIG. 3 is a schematic view of the membrane electrode assembly of the embodiments of the instant disclosure.

The electrolyzing tank 102 is communicated to the pure water supply device 20 for receiving pure water. The electrolytic gas generator 10 further comprises a membrane electrode assembly 104 disposed in the electrolyzing tank 102. Please refer to FIG. 3. FIG. 3 is a schematic view of the membrane electrode assembly of the embodiments of the instant disclosure. The membrane electrode assembly 104 comprises an anode 104a, a cathode 104b and a proton exchange membrane 104c disposed between the anode 104a and the cathode 104b. In the present embodiment, the cathode 104b is platinum (Pt)/carbon black optionally coated on a carbon cloth. The materials for forming the anode 104a are related to the type of gases generated thereby and are described later.

The adjustable power supply 101 is electrically connected to the anode 104a and the cathode 104b for forming an electric circuit. When performing electrolysis, the adjustable power supply 101 provides a voltage value to the membrane electrode assembly 104 for electrolyzing water in the electrolyzing tank 102, thereby generating a first gas and a second gas at the anode 104a and the cathode 104b respectively. The second gas is hydrogen gas.

The material constituting the anode 104a comprises an additive and a composition, in which the composition comprises perfluorinated sulfonic acid resin (Nafion), polytetrafluoroethylene (PTFE), sulfuric acid ($H_2SO_4$), carbon nanotubes and graphene.

The additive of the anode 104a and the voltage value applied to the membrane electrode assembly 104 are selected based on the first gas to be generated. For example, when the first gas generated at anode 104a is oxygen gas, the voltage value is less than 2.0 V and the additive of the anode 104a is a catalyst that assists the generation of hydrogen gas and oxygen gas, such as iridium, iridium black, iridium oxide, ruthenium, ruthenium oxide, platinum, platinum iridium, palladium, iridium ruthenium oxide, iridium-ruthenium-tantalum oxide, and any combination thereof.

In another embodiment, when the gas generated at the anode 104a comprises oxygen gas and ozone, the voltage value must be larger than 2.0 V, and the additive of the anode 104a is a catalyst that assists the generation of ozone such as tin-antimony-nickel alloy, lead dioxide, glassy carbon, boron doped diamond, platinum tantalum oxide and any combination thereof.

In the embodiments of the instant disclosure, the control unit 30 is electrically connected to the adjustable power supply 101, and a user can adjust the type of gases generated by the electrolytic gas generator 10 by controlling the voltage value provided by the adjustable power supply 101 through the control unit 30. In other words, by adjusting the voltage value of the electrolytic gas generator 10 through the control unit 30 and selecting different anodes 104a, the user can control the first gas generated at the anode 104a to be oxygen gas or a mixed gas containing oxygen gas and ozone.

In addition, wherein the first gas contains oxygen gas and ozone, the ratio of the concentrations of oxygen gas and ozone is related to the voltage value. When the voltage value increases, the ratio of the ozone concentration in the first gas increases. Therefore, the control unit 30 can control the ratio of the concentrations of oxygen gas and ozone by controlling the voltage value.

The first gas and the second gas generated by the anode 104a and the cathode 104b of the electrolytic gas generator 10 are transferred to the first gas storing unit 40 and the second gas storing unit 50 respectively for storing. After the electrolysis process, the second gas (hydrogen gas) generated at the cathode 104b is mixed with water and hence, the separator 103 is used for separating the second gas and water. The hydrogen gas separated from water is output to the second gas storing unit 50 through a pipeline for storing.

Please refer to FIG. 1. The first gas storing unit 40 is communicated to the electrolytic gas generator 10 and comprises an oxygen/ozone storing tank 401 and a first gas sensor 402. The first gas sensor 402 is disposed in the oxygen($O_2$)/ozone($O_3$) storing tank 401 for monitoring the concentration of oxygen gas and ozone in the oxygen($O_2$)/ozone($O_3$) storing tank 401. In addition, the first gas sensor 402 is electrically connected to the control unit 30 for transmitting the concentrations of oxygen gas and ozone to the control unit 30.

The control unit 30 processes the concentration signals of oxygen and ozone transmitted by the first gas sensor 402 for obtaining the ratio of the concentrations of oxygen gas and ozone in the oxygen($O_2$)/ozone($O_3$) storing tank 401, and based on the concentrations of oxygen gas and ozone, the control unit 30 judges whether or not the voltage value of the electrolytic gas generator 10 should be adjusted. For example, when the ratio of the concentrations of oxygen gas and ozone is lower than a first predetermined value, the control unit 30 controls the voltage value to be less than 2.0 V to increase the output of oxygen gas, thereby increasing the concentration of oxygen gas in the oxygen($O_2$)/ozone ($O_3$) storing tank 401. When the ratio of the concentrations of oxygen gas and ozone is larger than a second predetermined value, the control unit 30 controls the voltage value to be larger than 2.0 V to increase the output of ozone, thereby increasing the concentration of ozone.

Similarly, the second gas storing unit 50 comprises a hydrogen gas storing tank 502 and a second gas sensor 501, in which the second gas sensor 501 is disposed in the hydrogen gas storing tank 502 for monitoring the concentration of hydrogen gas. The second gas detector 501 is also electrically connected to the control unit 30 and provides feedback of the measured hydrogen gas concentration to the control unit 30. In addition, the control unit 30 can show the concentration of the hydrogen gas and the ratio of the concentrations of oxygen gas and ozone through a display unit (not shown). Therefore, the user can monitor the concentration of the hydrogen gas in the hydrogen gas storing tank 502 and the ratio of the concentrations of oxygen gas and ozone in the oxygen($O_2$)/ozone($O_3$) storing tank 401.

The gas output unit 60 is communicated to the first gas storing unit 40 and the second gas storing unit 50. In the present embodiment, the gas output unit 60 has a first output end 60a, a second output end 60b and a third output end 60c, in which the first output end 60a is used for outputting the first gas, the second output end 60b is used for outputting a mixed gas, the third output end 60c is used for outputting the second gas. The mixed gas comprises the first gas and the second gas.

Specifically, the gas output unit 60 further comprises a first flow splitting control valve 601 and a second flow splitting control valve 602. The first flow splitting control valve 601 is connected between the first gas storing unit 40, the first output end 60a and the second output end 60b for controlling the amount of the first gas flowing toward the first output end 60a and the second output end 60b. The second flow splitting control valve 602 is connected between the second gas storing unit 50, the second output end 60b and the third output end 60c for controlling the amount of the second gas flowing toward the second output end 60b and the third output end 60c.

In addition, the gas output unit 60 comprises a confluence pipeline (not numbered), a third flow splitting control valve 603 and a drying tank 604. The confluence pipeline is communicated between the first flow splitting control valve 601, the second flow splitting control valve 602 and the third flow splitting control valve 603. The first flow splitting control valve 601 and the second flow splitting control valve 602 control the first gas and the second gas to flow toward the confluence pipeline respectively for forming the mixed gas. The mixed gas flows toward the third flow splitting control valve 603. The first flow splitting control valve 601 and the second flow splitting control valve 602 can control the amount of the first gas and the second gas respectively, thereby controlling the concentration ratio of the first gas and the second gas in the mixed gas.

The drying tank 604 is communicated between the third flow splitting control valve 603 and the second output end 60b. When the water in the mixed gas needs to be removed, the third flow splitting control valve 603 can control the mixed gas to pass through the drying tank 604, then the mixed gas flows into the second output end 60b. In the present embodiment, the third flow splitting control valve 603 is directly communicated to the second output end 60b through another bypass pipeline (not numbered). In other words, when the mixed gas does not need to undergo the water-removing process, the third flow splitting control valve 603 controls the mixed gas to directly flow into the second output end 60b through the bypass pipeline. The drying tank 604 and the bypass pipeline are optional components and can be selected according to actual need. The instant disclosure is not limited thereto.

In the embodiments of the instant disclosure, all of the first output end 60a, the second output end 60b and the third output end 60c have valves (not shown). The gas provided at different output ends can be used by the user according to actual medical use. For example, when the medical use is to prevent hearing impairment by hydrogen gas, the user can open the valve at the second output end 60b for outputting the second gas (hydrogen gas) from the second output end 60b. The concentration of hydrogen gas can be between 0.5 to 1.5%, and the flow rate is 2 liter (L) per minute.

When the medical use is to treat diabetes wounds with high pressure oxygen or ozone, the user can open the valve at the first output end 60a for outputting the first gas (oxygen gas or the mixed gas of oxygen gas and ozone).

In the embodiment of the present embodiment, the medical gas-liquid supply system 1 can further comprise a liquid output unit 70, the liquid output unit 70 is communicated to the first gas storing unit 40 and the second gas storing unit 50. In the present embodiment, the liquid output unit 70 and the gas output unit 60 are communicated to the first gas storing unit 40 and second gas storing unit 50 respectively through different pipelines. In other words, the first gas output by the first gas storing unit 40 can flow to the gas output unit 60 and the liquid output unit 70 through two pipelines respectively for providing different medical uses. Similarly, the second gas output by the second gas storing unit 50 flows to the gas output unit 60 and the liquid output unit 70 through another two pipelines respectively.

The liquid output unit 70 comprises at least a first supplying end 70a, a second supplying end 70b and a third supplying end 70c. The first supplying end 70a is for outputting a mixed solution, in which the mixed solution has the first gas and the second gas dissolved therein. When the first gas is oxygen gas, the mixed solution is an aqueous solution containing hydrogen gas and oxygen gas. When the first gas is the mixed gas of oxygen gas and ozone, the mixed solution is an aqueous solution containing hydrogen gas, oxygen gas and ozone.

Specifically, the liquid output unit 70 further comprises a fourth flow splitting control valve 701, a first water-gas mixing device 704, a fifth flow splitting control valve 702, a second water-gas mixing device 703 and a mixing tank 705.

The fourth flow splitting control valve 701 is connected between the first gas storing unit 40, the first water-gas mixing device 704 and the mixing tank 705 for controlling the amount of the first gas flowing into the first water-gas mixing device 704 and the mixing tank 705 respectively. The fifth flow splitting control valve 702 is connected between the second gas storing unit 50, the mixing tank 705 and the second water-gas mixing device 703 for controlling the amount of the second gas flowing into the second water-gas mixing device 703 and the mixing tank 705 respectively.

In addition, the first water-gas mixing device 704, the second water-gas mixing device 703 and the mixing tank 705 are communicated to the first supplying end 70a, the second supplying end 70b and the third supplying end 70c.

In other words, when the first gas is output to the liquid output unit 70 from the first gas storing unit 40, the first gas passes through the fourth flow splitting control valve 701 and flows toward the first water-gas mixing device 704. The first water-gas mixing device 704 mixes the first gas with water supplied into the first water-gas mixing device 704 and forms an oxygen-rich water or ozone-rich water to provide to the first supplying end 70a.

Similarly, when the second gas is output to the liquid output unit 70 from the second gas storing unit 50, the second gas passes through the fifth flow splitting control valve 702 and flows toward the second water-gas mixing device 703. The second water-gas mixing device 703 mixes the second gas with water supplied into the second water-gas mixing device 703 and forms a hydrogen-rich water which is provided to the second supplying end 70b. In an embodiment, the water supplied to the first water-gas mixing device 704 and the second water-gas mixing device 703 is supplied by the pure water supply device 20.

In addition, the fourth flow splitting control valve 701 and the fifth flow splitting control valve 702 can control the first gas and the second gas to flow toward the mixing tank 705 concurrently, the first gas and the second gas mix with each other and are dissolved in the liquid in the mixing tank 705 for forming a mixed solution. The fourth flow splitting control valve 701 and the fifth flow splitting control valve 702 control the amount of the first gas and the second gas flowing into the mixing tank 705 for controlling the concentrations of the first gas and the second gas in the mixed solution according to different medical uses. The mixing tank 705 is communicated to the third supplying end 70c for outputting the mixed solution through the third supplying end 70c.

Please refer to Table 1. Table 1 shows the use of different medical gases and liquids. As shown in the table, different gases are suitable for treating different diseases. The medical gas-liquid supply system 1 provided by the embodiments of the instant disclosure allows the user to select and use the suitable gas or liquid through different output ends or supplying ends.

TABLE 1

|  | diabetes | cardiovascular disease | spinal nerve | hearing |
|---|---|---|---|---|
| hydrogen gas | — | — | — | 0.5~1.5% 2 L/min |
| hydrogen-rich water | — | 10 mg 0.6 mmol/L | 5 ml 0.6 mmol/L | — |
| oxygen gas | 100% 2.4ATM | 100% 2ATA | 100%, 2.4ATA | 100%, 250 kpa |
| ozone | 50 ppm 10 mg, 60 ppm | 40 ppm 200 ml | 30 ppm 10 ml | 75 ppm 0.7 mg |
| mixed solution | 900 ml(hydrogen gas 1.1~1.3 ppm, oxygen gas 0.6~1.0 ppm) | — | — | — |

As shown in Table 1, when there is a need to use the high pressure oxygen for treating wounds related to diabetes, the control unit 30 controls the voltage value of the electrolytic gas generator 10 to be less than 2.0 V for generating oxygen gas and hydrogen gas (i.e., the first gas is oxygen gas and the second gas is hydrogen gas). In addition, the control unit 30 controls the first flow splitting control valve 601 for outputting oxygen gas from the first output end 60a of the gas output unit 60.

When there is a need to use a mixed solution containing 1.1-1.3 ppm of hydrogen gas and 0.6-1.0 ppm oxygen gas to assist in the treatment of diabetes, the control unit 30 receives the command of the user and controls the fourth flow splitting control valve 701 and the fifth flow splitting control valve 702 for inputting hydrogen gas and oxygen gas of a predetermined amount into the mixing tank 705, the hydrogen gas and oxygen gas are mixed with each other and dissolved in the liquid in the mixing tank 705, and the third supplying end 70c outputs a mixed solution having hydrogen gas and oxygen gas with predetermined concentrations.

In addition, when there is a need to use ozone to assist in the treatment of the legs of a diabetes patient, the control unit 30 controls the voltage value of the electrolytic gas generator 10 to be larger than 2.0 V for generating oxygen gas, ozone and hydrogen gas (i.e., the first gas comprises oxygen gas and ozone, the second gas is hydrogen gas). In addition, the control unit 30 controls the ratio of concentrations of oxygen gas and ozone in the first gas by controlling the voltage value.

In sum, the medical gas-liquid supply system 1 provided by the embodiments of the instant disclosure utilizes the proton exchange membrane electrolytic gas generator to generate oxygen and ozone having relatively high purity. Besides, by controlling the voltage value during the electrolysis of water and, specifically, selecting the materials of the anode, the user can control the type of gases generated by the electrolytic gas generator. In addition, the medical gas-liquid supply system 1 provided by the embodiments of the instant disclosure can control the ratio of the concentrations of different gases in the mixed gas and mixed solution by controlling the first to fifth flow splitting control valves.

The above-mentioned descriptions represent merely the exemplary embodiment of the present disclosure, without any intention to limit the scope of the instant disclosure thereto. Various equivalent changes, alterations or modifications based on the claims of the instant disclosure are all consequently viewed as being embraced by the scope of the instant disclosure.

What is claimed is:

1. A medical gas-liquid supply system, comprising:
   an electrolytic gas generator;
   a pure water supply system connected to the electrolytic gas generator for supplying water to the electrolytic gas generator;
   a control unit electrically connected to the electrolytic gas generator, wherein the control unit controls the voltage value of the electrolytic gas generator for controlling the type of gases generated by the electrolytic gas generator;
   a first gas storing unit communicated to the electrolytic gas generator for storing a first gas output by the electrolytic gas generator;
   a second gas storing unit communicated to the electrolytic gas generator for storing a second gas output by the electrolytic gas generator; and
   a gas output unit communicated to the first gas storing unit and the second storing unit, wherein the gas output unit has a first output end for outputting the first gas, a second output end for outputting a mixed gas and a third output end for outputting the second gas, wherein the mixed gas comprises the first gas and the second gas.

2. The medical gas-liquid supply system according to claim 1, wherein the gas output unit further comprises a first flow splitting control valve, and the first flow splitting control valve is connected between the first gas storing unit, the first output end and the second output end for controlling the amount of the first gas flowing toward the first output end and the second output end.

3. The medical gas-liquid supply system according to claim 1, wherein the gas output unit further comprises a second flow splitting control valve, and the second flow splitting control valve is connected between the second gas storing unit, the second output end and the third output end for controlling the amount of the second gas flowing toward the second output end and the third output end.

4. The medical gas-liquid supply system according to claim 1, wherein when the voltage value is smaller than 2.0 V, the first gas is oxygen gas and the second gas is hydrogen gas, and when the voltage value is larger than 2.0 V, the first gas comprises oxygen gas and ozone, and the second gas is hydrogen gas.

5. The medical gas-liquid supply system according to claim 4, further comprises a liquid output unit, wherein the liquid output unit is connected to the first gas storing unit and the second gas storing unit, wherein the liquid output unit comprises a first supplying end, a second supplying end and a third supplying end, the first supplying end is configured to output an oxygen-rich water or an ozone-rich water, the second supplying end is configured to output a hydrogen-rich water, and the third supplying end is configured to output a mixed solution.

6. The medical gas-liquid supply system according to claim 5, wherein the liquid output unit further comprises:
a first water-gas mixing device communicated between the first supplying end and the first gas storing unit, wherein the first water-gas mixing device receives the first gas and generates the oxygen-rich water or the ozone-rich water;
a second water-gas mixing device communicated between the second supplying end and the second gas storing unit, wherein the second water-gas mixing device receives the second gas and generates the hydrogen-rich water; and
a mixing tank communicated to the third supplying end, the first gas storing unit and the second gas storing unit for receiving the first gas and the second gas to form the mixed solution.

7. The medical gas-liquid supply system according to claim 6, wherein the liquid output unit comprises a fourth flow splitting control valve, and the fourth flow splitting control valve is connected between the first gas storing unit, the mixing tank and the first water-gas mixing device for controlling the amount of the first gas flowing into the first water-gas mixing device and the mixing tank respectively.

8. The medical gas-liquid supply system according to claim 6, wherein the liquid output unit comprises a fifth flow splitting control valve, and the fifth flow splitting control valve is connected between the second gas storing unit, the mixing tank and the second water-gas mixing device for controlling the amount of the second gas flowing into the second water-gas mixing device and the mixing tank respectively.

9. The medical gas-liquid supply system according to claim 1, wherein the electrolytic gas generator comprises:
an electrolyzing tank communicated to the pure water supply device;
a membrane electrode assembly disposed in the electrolyzing tank, wherein the membrane electrode comprises an anode, a cathode and a proton exchange membrane, wherein the proton exchange membrane is disposed between the anode and the cathode; and
an adjustable power supply electrically connected to the anode and the cathode for forming an electric circuit, wherein the control unit is electrically connected to the adjustable power supply for controlling the voltage value provided by the adjustable power supply.

10. The medical gas-liquid supply system according to claim 9, wherein the anode comprises an additive and a composition, wherein when the first gas is oxygen gas, the additive is iridium, iridium black, iridium oxide, ruthenium, ruthenium oxide, platinum, platinum-iridium, palladium, iridium-ruthenium oxide, iridium-ruthenium-tantalum oxide or the combination thereof, and the composition comprises perfluorinated sulfonic acid resin, polytetrafluoroethylene, sulfuric acid and carbon nanotubes, and the voltage value is less than 2.0 V.

11. The medical gas-liquid supply system according to claim 9, wherein the anode comprises an additive and a composition, wherein when the first gas is ozone and oxygen, the additive is tin-antimony-nickel alloy, lead dioxide, glassy carbon, boron doped diamond, platinum-tantalum oxide or the combination thereof, and the composition comprises perfluorinated sulfonic acid resin, polytetrafluoroethylene, sulfuric acid and carbon nanotubes, and the voltage value is larger than 2.0 V.

12. The medical gas-liquid supply system according to claim 1, wherein the first gas storing unit further comprises a first gas sensor electrically connected to the control unit for detecting the concentration of the first gas and providing feedback to the control unit.

13. The medical gas-liquid supply system according to claim 1, wherein the second gas storing unit further comprises a second gas sensor electrically connected to the control unit for detecting the concentration of the second gas and providing feedback to the control unit.

* * * * *